United States Patent [19]

Turner

[11] Patent Number: 5,571,721

[45] Date of Patent: Nov. 5, 1996

[54] IMPROVED BIOLOGICAL CULTURE SLIDE AND METHOD OF MAKING SAME

[75] Inventor: Bruce R. Turner, Fremont, N.H.

[73] Assignee: Erie Scientific Company, Portsmith, N.H.

[21] Appl. No.: 238,312

[22] Filed: May 5, 1994

[51] Int. Cl.$^6$ ..................................................... C12M 1/00
[52] U.S. Cl. .................................. 435/305.1; 435/305.2; 435/305.4; 422/102; 359/398
[58] Field of Search .................................. 435/284, 285, 435/296, 297, 298, 299–301, 809, 288.1–288.4, 288.7, 304.1–305.4; 422/102, 104; 359/398

[56] References Cited

U.S. PATENT DOCUMENTS

| | | |
|---|---|---|
| 3,726,764 | 4/1973 | White . |
| 3,726,767 | 4/1973 | White .......................................... 435/301 |
| 3,745,091 | 7/1973 | McCormick ............................. 435/301 |
| 3,883,398 | 5/1975 | Ono .......................................... 435/301 |
| 4,299,920 | 11/1981 | Peters ....................................... 435/299 |
| 4,682,890 | 7/1987 | de Macario et al. ..................... 435/300 |

Primary Examiner—William Beisner
Attorney, Agent, or Firm—Wood, Herron & Evans, P.L.L.

[57] ABSTRACT

A culture slide kit for use in growing or differentiating various cell and tissue cultures, wherein the kit comprises a slide, a compartment and a bonding element. The compartment has sidewalls with an upper extremity and a lower margin, and is adapted to be operatively positioned on the upper surface of the slide. The bonding element is adapted to seal and releasably adhere the lower margin of the compartment sidewalls to the upper surface of the slide. Furthermore, the bonding element exhibits a greater bond strength with the compartment sidewall lower margin than with the upper surface of the slide, so that when the compartment is separated from the slide, substantially all of the adhesive is effectively removed from the slide.

32 Claims, 2 Drawing Sheets

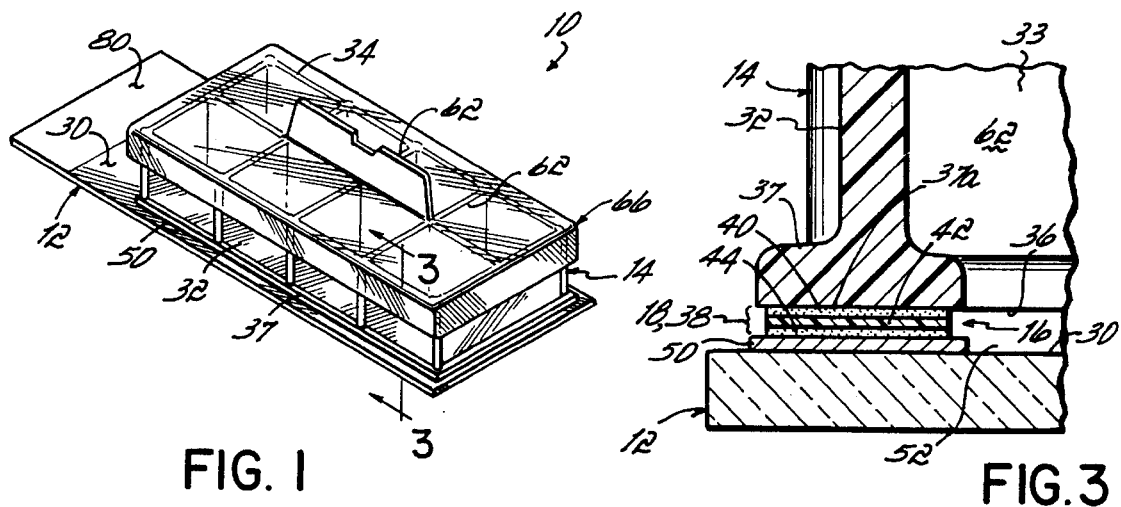
FIG. 1
FIG. 3
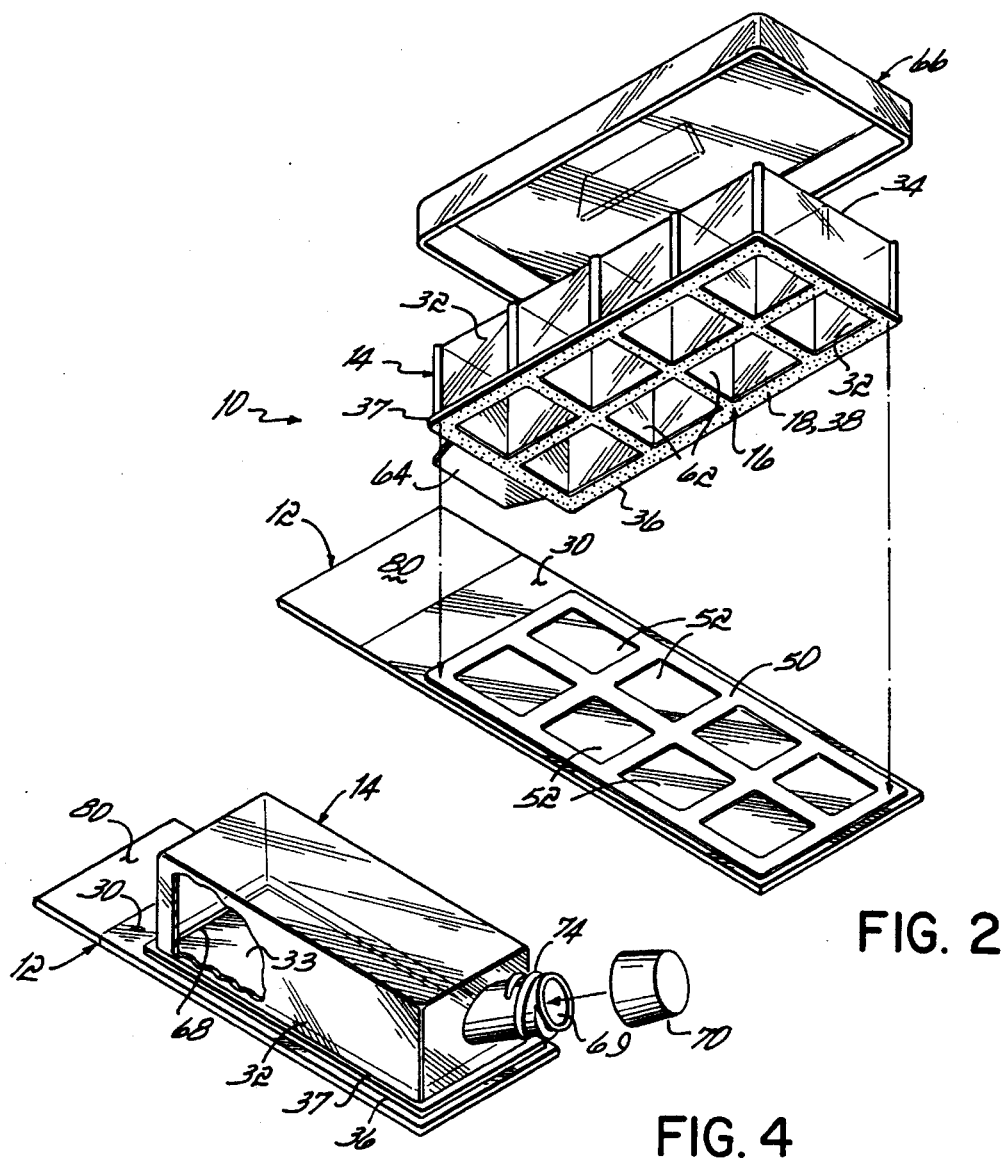
FIG. 2
FIG. 4

IMPROVED BIOLOGICAL CULTURE SLIDE AND METHOD OF MAKING SAME

FIELD OF THE INVENTION

This invention relates to microbiological culture slides for growing cells or tissue in a growth media, to be subsequently examined under a microscope. More particularly, the invention is directed to a culture slide kit wherein the kit has a slide and a compartment releasably adhered to the slide and sealed with respect thereto using a combined bonding and sealing element.

BACKGROUND OF THE INVENTION

Culture slides are used in biological research and in medical laboratory practice to grow or differentiate various cell and tissue cultures. These culture slides include a compartment having a single chamber or multiple discrete chambers in which the cultures may be grown. The chamber forms a reservoir which holds the mixture of cells or tissue and culture medium, while the slide forms a support surface to which the cultured cells or tissue may adhere.

As the culture process advances, progress may be monitored by viewing the cells from the bottom of the slide with the aid of an inverted microscope. When the culture has reached the desired state, the culture media is removed and the chamber is pulled from the slide and discarded, leaving the cells attached to the slide in an undisturbed state and ready for subsequent testing.

White U.S. Pat. No. 3,726,764 (the '764 patent) discloses a microbiological chamber apparatus having a box-like receptacle or compartment releasably adhered to a base member or slide. The compartment is releasably adhered to the slide using an adhesive gasket material such as the organopolysiloxane elastomer composition marketed by the General Electric Company under the designation RTV 630.

In order to adhere the compartment to the slide, the compartment base is held against the upper side of the slide using a clamping means, while an adhesive gasket material in a liquid or slurry form is injected into an injection port near the base of the compartment. The injection port is formed by a conduit located in a peripheral flange surrounding the bottom of the compartment. The internal passage of the conduit extends through the flange and into a rectangular groove formed in the bottom surface of the flange, with the rectangular groove being in general alignment with the sidewalls of the compartment. When the adhesive gasket material is injected into the injection port, the material fills the rectangular groove and contacts the slide in a pattern corresponding to the groove. The gasket material is then allowed to solidify, creating a liquid-impermeable seal between the compartment and the slide. Once the injected gasket material has solidified, the compartment is releasably adhered to the slide, and the clamping means may be removed. When the compartment is removed from the slide, the adhesive gasket remains adhered to the slide, and in combination with the upper surface of the slide, defines a well or wells upon which the cultures have grown.

Unfortunately, the microbiological chamber apparatus taught by the '764 patent has several disadvantages in use. For example, when the compartment is adhered to the slide the silicone present in the adhesive gasket material sometimes leaches onto the floor of the well on the upper surface of the slide, creating a surface which may not be conducive to growth of certain types of cell lines. The adhesive gasket material also poses some problems when the compartment is removed from the slide. As noted above, the adhesive remains adhered to the slide when the compartment is removed. Because some fixatives eat away at the gasket material, causing additional leaching and contamination of the cultures, it sometimes is desirable to remove the gasket material prior to fixing the cultures. However, removal of the gasket produces a bio-hazard. As the gasket is pulled off using forceps or the like, this removal step produces an aerosol effect, sending cell and tissue cultures up into the air. Furthermore, this cumbersome removal process takes additional lab time and may also disturb the various cultures adhering to the upper surface of the slide.

Therefore, it is desirable to have a culture slide in which the compartment may be releasably adhered and sealed to the slide without having an adhesive/sealant that leaches onto the floor of the well contaminating the cultures, or that leaves a gasket-forming sealant on the slide, which must be removed in some applications, thereby exposing the user to a bio-hazard and adding an additional step requiring additional lab time.

SUMMARY OF THE INVENTION

This invention is directed to a culture slide kit and a method of making such a kit, wherein the kit comprises a slide, a compartment, and a bonding element adapted to releasably adhere and seal the compartment to the slide. The compartment has sidewalls an upper extremity and a lower margin, and is adapted to be operatively positioned on the upper surface of the slide. The bonding element is adapted to seal and releasably bond the lower margin of the compartment to the upper surface of the slide, such that the bonding element remains bonded to the lower margin of the compartment when the compartment and slide are physically separated, leaving the upper surface of the slide substantially free of the bonding element following the separation.

Preferably, the bonding element is an adhesive adapted to seal and releasably adhere the lower margin of the compartment to the upper surface of the slide. The adhesive/sealant preferably is a multi-layer film comprising a polyester carrier film, a first acrylic adhesive layer on one side of the polyester carrier film and a second acrylic adhesive layer on the other side of the polyester carrier film. The first acrylic adhesive layer contacts the lower margin of the compartment, and the second acrylic adhesive layer is adapted to contact the upper surface of the slide. The adhesion of the second layer to the upper surface of the slide is less than i) the second layer's adhesion to the carrier film, and ii) the adhesion of the first layer to the carrier film and to the lower margin of the compartment. Typically, the acrylic adhesive layers are made of a solvent-based acrylic. Preferably, the polyester carrier film has a thickness of from about 0.5 mm to about 3 mm and each of the acrylic adhesive layers has a thickness of from about 0.5 mm to about 3 mm. More preferably, the polyester carrier film has a thickness of about 1 mm, the first acrylic adhesive layer has a thickness of about 3 mm and the second acrylic adhesive layer has a thickness of about 2 mm. Preferably, for convenience of assembly of the chamber slide kit, the adhesive is pressure sensitive.

The bonding element may take a variety of forms. One illustrative example includes a bond element comprising an adhesive and a longitudinal channel integral with the compartment lower margin. The channel has an interior surface, with the adhesive disposed within the channel in contact with the interior surface thereof and in contact with the upper surface of the slide. The adhesive chemically bonds to the channel interior as well as to the upper slide surface, sealing and adhering the chamber side wall to the upper slide surface. The bond strength between the adhesive and the interior channel surface is greater than the bond strength between the upper surface of the slide and the adhesive, whereby separation of the compartment from the slide effectively removes substantially all of the adhesive from the slide.

If desired, the bond element can additionally include serrations, grooves or projections on the interior surfaces of the channel, for establishing a mechanical bond between the adhesive and the interior surface of the channel which supplements the chemical bond therebetween, thereby increasing the bond strength between the lower margin of the chamber wall and the adhesive.

In one form of the invention, the slide may have a layer, preferably exhibiting both hydrophobic and release properties, adhered to its upper surface in a pattern which underlies the lower margin of the compartment when the compartment is operatively positioned on the upper surface of the slide. The adhesive exhibits stronger adhesion to the compartment lower margin than to the hydrophobic release layer, and the hydrophobic release layer exhibits stronger adhesion to the upper surface of the slide than to the adhesive. Therefore, separation of the compartment from the slide effectively removes substantially all of the adhesive from the slide, with substantially all of the hydrophobic release layer remaining adhered to the slide.

One of the advantages of the inventive culture slide kit is that, because the adhesive does not contain silicone, no undesirable material will leach onto the glass floor of the well, thereby avoiding the problems of contamination and related effects on cell growth.

A further advantage of the culture slide kit is that the adhesive and compartment are removed in one single step, in which virtually all of the adhesive is removed from the slide. Therefore, the inventive culture slide kit avoids the potentially dangerous and time-consuming additional step of removing gasket material remaining after separation of the chamber and slide.

These and other advantages will become apparent to one skilled in the art from the following detailed description of the invention and from the drawings.

BRIEF DESCRIPTION OF THE DRAWINGS

FIG. 1 is a perspective view of one embodiment of the culture slide kit;

FIG. 2 is an exploded perspective view of the embodiment of the culture slide kit shown in FIG. 1;

FIG. 3 is a vertical cross-section view taken along line 3—3 of FIG. 1 showing in an exaggerated format a detail of the junction of the compartment wall and upper slide surface; and FIG. 4 is a perspective view of another embodiment of the culture slide kit.

DETAILED DESCRIPTION OF THE INVENTION

Figure 5A:
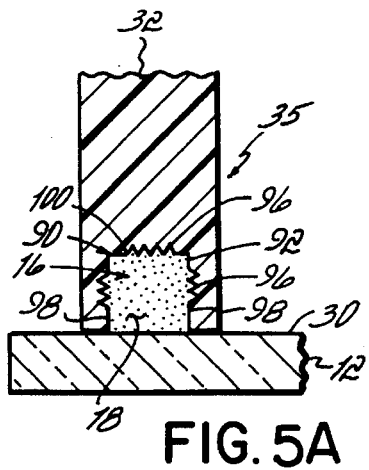
FIGS. 5A–5F are schematic cross-section views showing alternative embodiments of the bonding element bonding the compartment lower margin to the upper surface of the slide.

A preferred embodiment of a culture slide kit incorporating the principles of the present invention is shown in FIGS. 1–3. The kit 10 includes a slide 12, a compartment 14 and a bonding element 16 (FIG. 3) adapted to releasably adhere the compartment 14 to the slide 12. The compartment 14 has sidewalls 32, an upper extremity or edge 34 and a lower margin 35, and the slide 12 has an upper surface 30. The bonding element 16 includes an adhesive 18, as well as the surface region 37A of flange 37 of the compartment lower margin 35 which is in contact with the adhesive 18. The adhesive 18 is applied between the flange surface 37A of flange 37 formed on the compartment lower margin 35, and the upper surface 30 of the slide 12. The adhesive chemically bonds to both surfaces 37A and 30 to releasably adhere and seal the compartment 14 to the upper surface 30 of the slide 12.

The bonding element 16 may take a variety of forms as described in detail hereafter. However, a feature common to each of these different bond elements is that the bonding element releasably seals and bonds the compartment to the slide. Another common feature is that, when the compartment is physically separated from the slide, substantially all of the bond element remains with the compartment, leaving the slide upper surface substantially free of any bond element. This second feature results because the bond strength between the bond element and the compartment is greater than the bond strength between the bond element and the slide. The bond strength between the bond element and the compartment is the sum of the bond strengths provided by any chemical bond between the adhesive and compartment, and any mechanical bond between the adhesive and compartment. The bond strength between the adhesive and the slide also is the sum of any chemical and mechanical bonds therebetween, but most typically, the adhesive-to-slide bonding will be solely of the chemical type.

As noted above, in the preferred embodiment depicted in FIGS. 1–3, the bonding element 16 includes, in addition to the adhesive 18, the lower surface 37A of the flange 37. The flange 37 extends both outwardly and inwardly from the lower edges 36 of the lower margin 35 of the sidewalls 32 as best shown in FIGS. 2 and 3. The flange 37 slightly increases the surface area of the compartment wall lower edges 36, thereby enhancing the releasable seal created by the adhesive 18 disposed between the compartment lower edges 36 and the slide 12. However, if desired, the lower edges 36 may have a width equal to the width of the sidewalls 32.

Preferably the adhesive is pressure sensitive. This renders more convenient the assembly of the compartment to the slide during fabrication. While the preferred embodiment incorporates a pressure sensitive adhesive, in which the application of pressure initiates the bonding of the adhesive, other adhesives can be used such as thermally-cured, light-cured, ultrasonically cured, and the like.

In the preferred embodiment, the pressure sensitive adhesive 16 is a multilayer film 38 as shown in FIG. 3. The multilayer film 38 includes a polyester carrier film 42 sandwiched between a first acrylic adhesive layer 40 and a second acrylic adhesive layer 44. The first acrylic adhesive layer 40 is bonded to the lower edges 36 of the compartment 14, with the second acrylic adhesive layer 44 being the outermost layer, adapted to releasably adhere to the upper surface 30 of the slide 12. The thickness of the multilayer film 38 may be varied, and preferably, each of the polyester carrier film 42, first acrylic adhesive layer 40 and second acrylic adhesive layer 44 has a thickness of from about 0.5 mm to about 3 mm. More preferably, the polyester carrier film 42 has a thickness of about 1 mm, the first acrylic adhesive layer 40 has a thickness of about 3 mm and the second acrylic adhesive layer 44 has a thickness of about 2 mm. The adhesive may be any of a number of different solvent-based acrylic adhesives inert to and impermeable to aqueous solutions and standard tissue culture media, such as the acrylic adhesives available from Coating Sciences, Inc. in Bloomfield, Conn. under the product designation S268.

The preferred embodiment of the invention further includes a layer 50, preferably exhibiting both hydrophobic and release properties, adhered to the upper surface 30 of the slide 12 in a pattern which underlies the lower margin 35 of the compartment 14 when the compartment 14 is operatively positioned on the upper surface 30 of the slide 12 as shown in FIGS. 2 and 3. Preferably, the layer 50 is comprised of a fluorinated hydrocarbon-filled ink, and more preferably, the layer 50 is a polytetrafluoroethylene-filled ink as is available from Cell Line, Inc., in New Field, N.J. or Erie Scientific Company in Portsmouth, N.H. The layer 50, in combination with the upper surface 30 of the slide 12, defines a discrete well or wells 52 as shown in FIGS. 2 and 3.

The preferred embodiment has been described in connection with the use of an inert and impervious hydrophobic layer which also serves as a release layer to assist in providing an adhesive-free slide upon separation of the chamber from the slide. If desired, an inert and impervious release layer which is not hydrophobic in nature may be used on the upper slide surface underlying the lower margin of the compartment wall.

The bonding element 16 is able to releasably seal the compartment 14 to either a hydrophobic release layer 50 on the upper surface 30 of the slide 12 or directly to the upper surface 30 of the slide 12 without a hydrophobic release layer 50. In either case, when the compartment 14 is removed from the slide 12 the bonding element 16 remains bonded to the lower margin 35 of the compartment 14, leaving the hydrophobic release layer 50 or the plain upper surface of the slide 12 virtually free of any adhesive 18. The bonding element 16 remains with the compartment 14 because the adhesive 18 exhibits a stronger adhesion to the compartment 14 than to either the layer 50 or plain upper surface 30 of the slide 12. When a slide 12 having the hydrophobic release layer 50 is used, the layer 50 remains bonded to the upper surface 30 of the slide 12 because the layer 50 exhibits stronger adhesion to the slide 12 than to the adhesive 18.

The hydrophobic release layer 50 is preferred because it offers some additional benefits. For example, although the adhesive 18 creates an effective seal with either the layer 50 or the plain upper surface 30 of the slide 12, the adhesive 18 does not bond quite as strongly to the layer 50 as to the plain upper surface 30 of the slide 12. Therefore, when a slide 12 having the layer 50 is used, the compartment 14 may be removed more easily than when a slide 12 without the layer 50 is used.

Figure 5B:
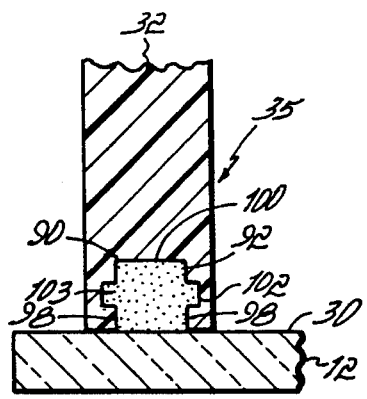
Figure 5C:
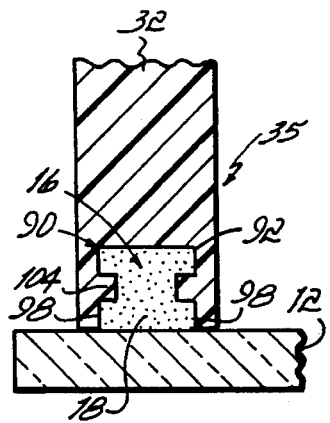
Figure 5D:
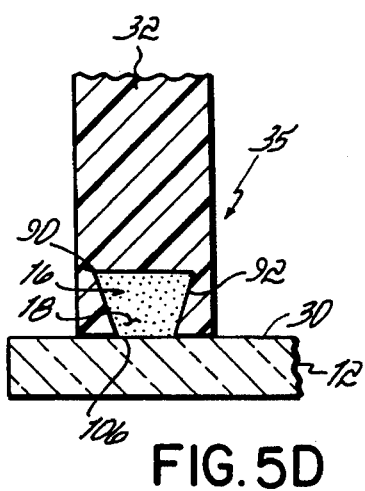
Figure 5E:
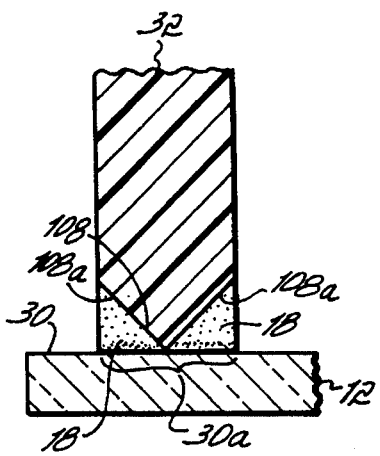
Figure 5F:
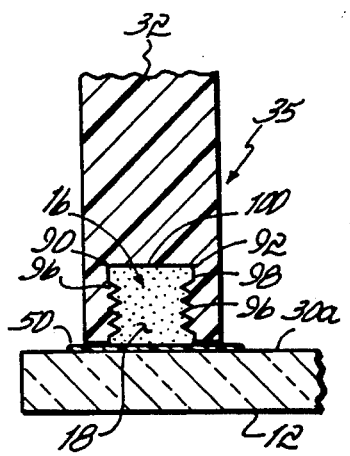

A few of the many other possible bonding element 16 configurations are shown in FIGS. 5A–5F. These figures are diagrammatic cross-sectional views showing a compartment sidewall 32 sealed and releasably adhered either directly to the upper surface 30 of a slide 12 (FIGS. 5A–5E) or to a hydrophobic release layer 50 on the upper surface 30 of the slide 12 (FIG. 5F). Note that any of the bonding elements depicted in FIGS. 5A–5F may be adhered either directly to the slide upper surface or to a hydrophobic release layer if such a layer is used.

Examples of bonding elements 16 using both chemical and mechanical bonds are shown in FIGS. 5A–5D. In these figures, the bonding element 16 includes an adhesive 18 and a longitudinal channel 90 integral with the compartment lower margin 35. The channel 90 has an interior surface 92 made up of two interior sidewalls 98 and a ceiling or upper interior sidewall 100. The interior sidewalls 98 have surface irregularities selected from the group of projections and indentations to facilitate the formation of mechanical bonds with the adhesive when it hardens. The adhesive 18 is disposed within the channel 90 in an unhardened condition, contacting and forming a chemical bond with the interior surface 92 and the upper surface 30 of the slide 12. In FIG. 5A, the unhardened adhesive also forms a mechanical bond with the projections, or serrations, 96 when the adhesive hardens. In FIG. 5B, when the adhesive hardens, a mechanical bond is created between the indentations, or grooves, 102 in the interior sidewalls 98 of interior channel surface 92 and adhesive 103 which penetrates the grooves. In FIG. 5C, the mechanical bond between adhesive 18 and interior surface 92 is created by channel wall projections 104 in the interior sidewalls 98 which extend into the adhesive 18 and are gripped thereby when the adhesive hardens.

FIG. 5D also shows a chemical and mechanical bond between the interior channel 90 formed in the margin 35 of the chamber wall 32 and the adhesive 18. The mechanical bond between adhesive 18 and channel 90 is created by the formation of a dovetail groove 106 having a reduced neck 106A which serves to grip the adhesive 18 once it hardens. The upwardly and outwardly sloping sidewalls create indentations relative to the necked portion 106A. The chemical bond between the adhesive 18 and channel 90 occurs at the interface between them, namely, at interior surface 92.

FIG. 5E shows an example of a bonding element 16 using solely chemical bonding. In this embodiment, the bonding element 16 includes an adhesive 18 and a V-shaped edge 108 integral with the compartment lower margin 35. The adhesive 18 chemically bonds with the V-shaped surface 108A of the V-shaped edge 108 and with the underlying surface 30A of slide 12. When the compartment 14 is separated from the slide 12, because the adhesive 18 forms a greater chemical bond strength with the V-shaped edge surface 108A than with the lesser surface area upper slide surface 30A, the adhesive remains adhered to the lower margin 35 of the chamber wall, leaving the slide surface free of adhesive residue. The greater bond strength may result from the adhesive 18 having a greater surface area of contact with the V-shaped edge 108 than with the slide upper surface 30, and/or the adhesive 18 having a greater chemical bonding affinity for the material used in the compartment 14 than in the slide 12.

FIG. 5F is an example of a bonding element 16 using principally only mechanical bonding. In this example, the bonding element 16 includes an adhesive 18 and a channel 90. The channel 90 has an interior surface 92 formed by two interior sidewalls 98 and an upper interior wall 100, with each of the interior sidewalls 98 having serrations 96. In this particular example, the adhesive 18 is an RTV silicone or other similar adhesive having very little chemical bonding affinity to the wall 32 of compartment 14 which is made of polystyrene or another similar material. Although the RTV silicone adhesive 18 forms a chemical bond with hydrophobic release layer 50 adhered to the slide upper surface 30, a mechanical bond must be used to bond the adhesive 18 with the interior surface 92 of the channel 90. In this embodiment, this mechanical bonding is accomplished by the serrations 96, which serve to grip the RTV silicone adhesive 18. The mechanical bond between the hardened silicone adhesive 18 and serrations 96 exceeds the chemical bond between the adhesive and hydrophobic release layer 50.

For convenience and ease of manufacture, the adhesive 18 can be inserted into the channels 90 of the embodiments of FIGS. 5A–5D and 5F in any desired manner, such as shown in U.S. Pat. No. 3,726,764, in the name of F. K. White.

The compartment 14 made according to the principles of the inventive culture slide kit may come in several different forms and have different features. For example, the compartment 14 may have a single chamber (FIG. 4) or multiple chambers (FIGS. 1 and 2). Multiple chambers typically are created by having interior sidewalls 62 within the compartment 14 as shown in FIGS. 1 and 2. If desired, the compartment 14 also may include a tab 64, providing the user with a convenient place to grasp the compartment 14 when removing the compartment 14 from the slide 12 (FIG. 2). Additionally, the top surface of the compartment 14 may be open, in which case a removable cover 66 may be provided as shown in FIGS. 1 and 2. If desired, the removable cover 66 may have a grasping tab on a cover end-wall (not shown), similar to the tab 64 on the compartment 14, instead of the cover handle shown in FIGS. 1 and 2. This grasping tab may be used to assist the user in removing the compartment 14 while the cover 66 is on the compartment 14.

An alternative embodiment according to the principles of this invention, is shown in FIG. 4. In this form, the compartment 14 has a top wall 67 with sidewalls 32 depending therefrom and having lower edges 36. The top wall 67 and the upper extremity of the sidewalls 32 are integral and collectively define a covered compartment 14 having an open bottom 68. In order to access the chamber 33 when the compartment 14 is releasably adhered to the slide 12, the compartment 14 is provided with an access port 69 extending outwardly from one of the sidewalls 32 as shown in FIG. 4. Preferably, the access port 69 may be sealed using a device such as a closure cap 70 having threads (not shown) which engage threads 74 on the access port 69 (FIG. 4).

The compartment 14 may be made of any of a number of different plastics or glass which are inert to and impermeable to aqueous solutions and standard tissue culture media. Preferably, the compartment 14 is formed from a transparent thermoplastic, such as polystyrene, polypropylene, celluloid, polymethylmethacrylate, polymethacrylate and the like. More preferably, the compartment 14 is made of polystyrene.

The slide 12 may be made of a glass or plastic inert to and impermeable to aqueous solutions and standard tissue culture media. Preferably, soda glass is used. If desired, the slide 12 may be a slide 12 having a frosted coating 80 on an end of the upper surface 30, as is available from Erie Scientific Company, Portsmouth, N.H. The frosted coating allows for easy, permanent labeling of the slide.

The upper edge of compartment and cover could be provided with a complementary projection and recess (not shown), respectively, to enable the cover to be properly seated and re-seated on the compartment in only one orientation, which may be particularly useful for compartments having multiple chambers. In this way, if any material from an individual chamber or any material derived from the contents of that chamber is deposited on the corresponding inside surface of the cover (for example, a virus, bacteria, condensate, culture, etc.), it is not possible to re-seat the cover on the compartment in an orientation different than that which existed prior to removing the cover, which if permitted to occur could contaminate a given culture with material from another culture.

This invention is not limited to the description discussed above, but on the contrary is intended to cover the various modifications and equivalent arrangements included within the spirit and scope of the appended claims.

What is claimed is:
1. A culture slide kit, comprising:
(a) a slide having an upper surface;
(b) a compartment having sidewalls with an upper extremity and a lower margin, said compartment adapted to be operatively positioned on said upper surface of said slide; and
(c) a bonding element adapted to seal and releasably bond said upper surface of said slide to said lower margin, said bonding element including an acrylic adhesive and remaining bonded to said lower margin when said compartment and slide are physically separated, leaving said upper surface of said slide substantially free of said bonding element following said separation.

2. A culture slide kit, comprising:
(1) a slide having an upper surface;
(2) a compartment having sidewalls with an upper extremity and a lower margin, said compartment adapted to be operatively positioned on said upper surface of said slide; and
(3) a bonding element adapted to seal and releasably bond said upper surface of said slide to said lower margin, said bonding element including an adhesive and remaining bonded to said lower margin when said compartment and slide are physically separated, leaving said upper surface of said slide substantially free of said bonding element following said separation, said adhesive being a multilayer film comprising:
(a) a carrier film;
(b) a first adhesive layer on one side of said carrier film, said first adhesive layer contacting said lower margin; and
(c) a second adhesive layer on the other side of said carrier film, said second adhesive layer adapted to contact said upper surface of said slide, the adhesion of said second layer to said upper surface of said slide being less than i) said second layer's adhesion to said carrier film, and ii) the adhesion of said first layer to said carrier film and to said lower margin.

3. A culture slide kit as recited in claim 2, wherein said carrier film is a polyester carrier film, said first adhesive layer is an acrylic adhesive layer and said second adhesive layer is an acrylic adhesive layer.

4. A culture slide kit as recited in claim 3, wherein said acrylic adhesive layers are made of a solvent-based acrylic.

5. A culture slide kit as recited in claim 3, wherein said polyester carrier film has a thickness of from about 0.5 mm to about 3 mm and each of said acrylic adhesive layers has a thickness of from about 0.5 mm to about 3 mm.

6. A culture slide kit as recited in claim 3, wherein said polyester carrier film has a thickness of about 1 mm, said first acrylic adhesive layer has a thickness of about 3 mm, and said second acrylic adhesive layer has thickness of about 2 mm.

7. A culture slide kit as recited in claim 2, further comprising a layer located between said adhesive of said bonding element and said upper surface of said slide and being adhered to said upper surface of said slide in a pattern which underlies said lower margin when said compartment is operatively positioned on said upper surface of said slide, said bonding element adhesive exhibiting stronger adhesion to said lower margin than to said layer, said layer exhibiting stronger adhesion to said upper surface of said slide than to said bonding element adhesive, and said bonding element exhibiting a lesser adhesive affinity for said layer than for said upper surface of said slide, whereby said lesser adhesive affinity assists in the separation of said compartment from said slide, and whereby separation of said compartment from said slide effectively removes substantially all of said bonding element adhesive from said slide, with substantially all of said layer remaining adhered to said slide.

8. A culture slide kit as recited in claim 7, wherein said layer is hydrophobic.

9. A culture slide kit as recited in claim 8, wherein said hydrophobic layer is comprised of a fluorinated hydrocarbon-filled ink.

10. A culture slide kit as recited in claim 2, further comprising a cover adapted to fit over said upper extremity of said compartment.

11. A culture slide kit as recited in claim 2 wherein said adhesive is pressure sensitive.

12. A culture slide kit, comprising:

(a) a slide having an upper surface;

(b) a compartment having sidewalls with an upper extremity and a lower margin, said compartment adapted to be operatively positioned on said upper surface of said slide; and (c) a bonding element adapted to seal and releasably bond said upper surface of said slide to said lower margin, said bonding element including an adhesive and remaining bonded to said lower margin when said compartment and slide are physically separated, leaving said upper surface of said slide substantially free of said bonding element following said separation, said lower margin including a longitudinal channel, said channel having an interior surface, said adhesive disposed within said channel and contacting said interior surface and said upper surface of said slide, said adhesive forming a greater bond strength with said channel interior surface than with said upper surface of said slide, whereby separation of said compartment from said slide effectively removes substantially all of said adhesive from said slide, said adhesive being hardenable, and said channel interior surface including a surface irregularity to establish a mechanical bond between said adhesive and said surface irregularity when said adhesive hardens.

13. A culture slide kit as recited in claim 12, wherein said surface irregularity is selected from the group consisting of a projection, a serration, an indentation, a groove, a channel wall projection and combinations thereof.

14. A culture slide kit as recited in claim 12 wherein said of the adhesive for the lower margin is substantially less than the affinity of the adhesive for the slide, whereby the bond between the adhesive and the lower margin is substantially solely a mechanical bond, with the bond strength of the mechanical bond between the adhesive and the lower margin exceeding the bond strength of the chemical bond between the adhesive and the slide.

15. A culture slide kit, comprising:

(a) a slide having an upper surface;

(b) a compartment having sidewalls with an upper extremity and a lower margin, said compartment adapted to be operatively positioned on said upper surface of said slide; and (c) a bonding element adapted to seal and releasably bond said upper surface of said slide to said lower margin, said bonding element including an adhesive and remaining bonded to said lower margin when said compartment and slide are physically separated, leaving said upper surface of said slide substantially free of said bonding element following said separation, said lower margin including a longitudinal channel, said channel having an interior surface, said adhesive disposed within said channel and contacting said interior surface and said upper surface of said slide, said adhesive forming a greater bond strength with said channel interior surface than with said upper surface of said slide, whereby separation of said compartment from said slide effectively removes substantially all of said adhesive from said slide, said longitudinal channel having a cross-sectional shape approximating a dovetail groove having a necked region proximate the upper surface of the slide to establish a mechanical bond between the groove and hardened adhesive in the groove.

16. A culture slide kit, comprising:

(a) a slide having an upper surface;

(b) a compartment having sidewalls with an upper extremity and a lower margin, said compartment adapted to be operatively positioned on said upper surface of said slide; and (c) a bonding element adapted to seal and releasably bond said upper surface of said slide to said lower margin, said bonding element including an adhesive and remaining bonded to said lower margin when said compartment and slide are physically separated, leaving said upper surface of said slide substantially free of said bonding element following said separation, the lower margin having a surface area free of mechanical bond-forming surface irregularities which is in contact with the adhesive, the surface area of the lower margin in contact with the adhesive being greater than the surface area of the upper slide surface which is in contact with the adhesive, and wherein the lower margin is fabricated of a material exhibiting a lesser affinity for the adhesive than exhibited by the slide, whereby the bond between the adhesive and the lower margin is substantially solely a chemical bond and yet when the slide and compartment are separated, the adhesive remains adhered to the lower margin and releases from the slide.

17. A culture slide kit, comprising:

(a) a slide having an upper surface;

(b) a compartment having sidewalls with an upper extremity and a lower margin, said compartment adapted to be operatively positioned on said upper surface of said slide;

(c) a bonding element adapted to seal and releasably bond said upper surface of said slide to said lower margin, said bonding element remaining bonded to said lower margin when said compartment and slide are physically separated, leaving said upper surface of said slide substantially free of said bonding element following said separation; and (d) a layer located between said bonding element and said upper surface of said slide and being adhered to said upper surface of said slide in a pattern which underlies said lower margin of said compartment sidewalls when said compartment is operatively positioned on said upper surface of said slide, said bonding element exhibiting stronger adhesion to said lower margin than to said layer, said layer exhibiting stronger adhesion to said upper surface of said slide than to said bonding element, and said bonding element exhibiting a lesser adhesive affinity for said layer than for said upper surface of said slide, whereby said lesser adhesive affinity assists in the separation of said compartment from said slide, and whereby separation of said compartment from said slide effectively removes substantially all of said bonding element from said layer with substantially all of said layer remaining adhered to said slide.

18. A culture slide kit as recited in claim 17, wherein said layer is hydrophobic.

19. A culture slide kit as recited in claim 18, wherein said hydrophobic layer is comprised of a fluorinated hydrocarbon-filled ink.

20. A culture slide kit as recited in claim 17, wherein said slide, said compartment, said adhesive and said layer are inert to and impermeable to aqueous solutions and standard tissue culture media.

21. A method of making a culture slide kit, comprising the steps of:

(a) providing a microscope slide having an upper surface;

(b) providing a compartment having sidewalls with an upper extremity and a lower margin, the compartment adapted to be operatively positioned on the upper surface of the slide; and (c) providing a bonding element between the upper surface of the slide and the lower margin to seal and releasably bond the upper surface of the slide to the lower margin, the bonding element including an adhesive and remaining bonded to the lower margin when the compartment and slide are physically separated, leaving the upper surface of the slide substantially free of the bonding element following separation of the slide and compartment, said adhesive being a multilayer film comprising:
(1) a carrier film;
(2) a first adhesive layer on one side of the carrier film, the first adhesive layer contacting the lower margin; and
(3) a second adhesive layer on the other side of the carrier film, the second adhesive layer adapted to contact the upper surface of said slide, the adhesion of the second layer to the upper surface of the slide being less than i) the second layer's adhesion to the carrier film, and ii) the adhesion of the first layer to the carrier film and to the lower margin.

22. A method of making a culture slide kit as recited in claim 21, including prior to the sealing and bonding step the further step of adhering a layer to the upper surface of the slide in a pattern which underlies the lower margin when the compartment is operatively positioned on the upper surface of the slide, the adhesive exhibiting stronger adhesion to the lower margin than to the layer, the layer exhibiting stronger adhesion to the upper surface of the slide than to the adhesive, and said bonding element exhibiting a lesser adhesive affinity for said layer than for said upper surface of said slide, whereby said lesser adhesive affinity assists in the separation of said compartment from said slide, and whereby separation of the compartment from the slide effectively removes substantially all of the adhesive from the slide, with substantially all of the layer remaining adhered to the slide.

23. A method of making a culture slide kit as recited in claim 22, wherein the layer application step includes applying a hydrophobic layer.

24. A method of making a culture slide kit as recited in claim 23, wherein said hydrophobic layer is comprised of a fluorinated hydrocarbon-filled ink.

25. A method of making a culture slide kit as recited in claim 21, wherein said carrier film is a polyester carrier film, said first adhesive layer is an acrylic adhesive layer and said second adhesive layer is an acrylic adhesive layer.

26. A method of making a culture slide kit as recited in claim 25, wherein the acrylic adhesive layers are made of a solvent-based acrylic.

27. A method of making a culture slide kit as recited in claim 25, wherein the polyester carrier film has a thickness of from about 0.5 mm to about 3 mm and each of the acrylic adhesive layers has a thickness of from about 0.5 mm to about 3 mm.

28. A method of making a culture slide kit as recited in claim 25, wherein the polyester carrier film has a thickness of about 1 mm, the first acrylic adhesive layer has a thickness of about 3 mm, and the second acrylic adhesive layer has thickness of about 2 mm.

29. A method of making a culture slide kit, comprising the steps of:

(a) providing a microscope slide having an upper surface;

(b) providing a compartment having sidewalls with an upper extremity and a lower margin, the compartment adapted to be operatively positioned on the upper surface of the slide;

(c) providing a bonding element between the upper surface of the slide and the lower margin to seal and releasably bond the upper surface of the slide to the lower margin, the bonding element including an adhesive and remaining bonded to the lower margin when the compartment and slide are physically separated, leaving the upper surface of the slide substantially free of the bonding element following separation of the slide and compartment; and (d) providing a surface irregularity in the lower margin which is adapted to contact the adhesive in an unhardened condition, wherein the bonding element providing step includes introducing unhardened adhesive in contact with the surface irregularity to form a mechanical bond with the surface irregularity when the adhesive hardens and a chemical bond with the upper surface of the slide.

30. A method of making a culture slide kit as recited in claim 29, wherein the surface irregularity providing step includes providing a surface irregularity selected from the group consisting of a projection, a serration, an indentation, a groove, a channel wall projection and combinations thereof.

31. A method of making a culture slide kit as recited in claim 29, wherein the affinity of the adhesive for the lower margin is substantially less than the affinity of the adhesive for the slide, whereby the bond between the adhesive and the lower margin is substantially solely a mechanical bond, with the bond strength of the mechanical bond between the adhesive and lower margin exceeding the bond strength of the chemical bond between the adhesive and the slide.

32. A method of making a culture slide kit, comprising the steps of:

(a) providing a microscope slide having an upper surface;

(b) providing a compartment having sidewalls with an upper extremity and a lower margin, the compartment adapted to be operatively positioned on the upper surface of the slide; and (c) providing a bonding element between the upper surface of the slide and the lower margin of the compartment sidewalls to seal and releasably bond the upper surface of the slide to the lower margin of the compartment sidewalls, the bonding element including an adhesive and remaining bonded to the lower margin when the compartment and slide are physically separated, leaving the upper surface of the slide substantially free of the bonding element following separation of the slide and compartment, wherein the compartment providing step includes providing a compartment in which the lower margin has a surface area free of mechanical bond-forming surface irregularities which is in contact with the adhesive, the surface area of the lower margin in contact with the adhesive being greater than the surface area of the upper slide surface which is in contact with the adhesive, and wherein the lower margin is fabricated of a material exhibiting a lesser affinity for the adhesive than exhibited by the slide, whereby the bond between the adhesive and the lower margin is substantially solely a chemical bond and yet when the slide and compartment are separated, the adhesive remains adhered to the lower margin and releases from the slide.

* * * * *

UNITED STATES PATENT AND TRADEMARK OFFICE
CERTIFICATE OF CORRECTION

PATENT NO. : 5,571,721
DATED : November 5, 1996
INVENTOR(S) : Bruce R. Turner

It is certified that error appears in the above-indentified patent and that said Letters Patent is hereby corrected as shown below:

In the claims:

Column 9, line 46, "said"  should be --the affinity--

Signed and Sealed this

Seventeenth Day of June, 1997

Attest:

BRUCE LEHMAN

*Attesting Officer*   *Commissioner of Patents and Trademarks*